United States Patent [19]

Di Billa

[11] 4,096,333
[45] Jun. 20, 1978

[54] PROCESS FOR THE PREPARATION OF SUBSTITUTED INDAZOLES

[75] Inventor: Eugene P. Di Billa, Piscataway, N.J.

[73] Assignee: Tenneco Chemicals, Inc., Saddle Brook, N.J.

[21] Appl. No.: 691,693

[22] Filed: Jun. 1, 1976

Related U.S. Application Data

[60] Division of Ser. No. 541,673, Jan. 16, 1975, Pat. No. 3,988,347, which is a continuation-in-part of Ser. No. 504,400, Sep. 9, 1974, abandoned.

[51] Int. Cl.² .......................................... C07D 231/56
[52] U.S. Cl. .................................................. 548/371
[58] Field of Search ..................... 260/310 C; 548/371

[56] References Cited

U.S. PATENT DOCUMENTS

| 3,862,958 | 1/1975 | Ruechardt et al. | 260/310 C |
| 3,988,347 | 10/1976 | DiBella | 260/310 C |

OTHER PUBLICATIONS

Morrison et al., Organic Chemistry p. 557.
House, Modern Synthetic Organic Reactions, p. 429.

*Primary Examiner*—Natalie Trousof
*Assistant Examiner*—Jane T. Fan
*Attorney, Agent, or Firm*—Evelyn Berlow

[57] ABSTRACT

Substituted indazoles that have the structural formula

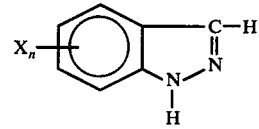

wherein X represents halogen, trihalomethyl, nitro, —SO₂R, cyano, acoyl, acoylamino, aroylamino, or —COOR'; R represents hydroxyl, halogen, alkyl, haloalkyl, alkylamino, phenyl, or substituted phenyl; R' represents hydrogen, halogen, alkyl, haloalkyl, phenyl, or substituted phenyl; and $n$ represents a number in the range of 1 to 4 are prepared by the direct nitrosation of the corresponding 2-methylacetanilide with an alkali metal nitrite or alkaline earth metal nitrite under conditions of controlled acidity in the presence of a dehydrating agent at a temperature in the range of 50°–120° C.

9 Claims, No Drawings

PROCESS FOR THE PREPARATION OF SUBSTITUTED INDAZOLES

This is a division of my copending application Ser. No. 541,673, which was filed on Jan. 16, 1975, now U.S. Pat. No. 3,988,347, and which is a continuation-in-part of application Ser. No. 504,400, which was filed on Sept. 9, 1974 and which has been abandoned.

This invention relates to a process for the production of indazoles. More particularly, it relates to an improved process for the production of indazoles that have certain substituents on the aromatic nucleus.

The preparation of indazole and substituted indazoles by the cyclization of N-nitroso-o-toluidines is well known. The preparation of indazole by heating N-nitrosobenzo-o-toluidine in boiling benzene was described by Jacobson and Huber in Ber. 41, 660 (1908). A similar approach using substituted N-nitroso-o-acetotoluidides was used by Auwers et al. (Ber. 55, 1139 (1922); Ann. 478, 154 (1930)) to prepare 5-chloroindazole and 5,7-dichloroindazole. In these processes, nitrogen oxides were used to effect nitrosation of the toluidides. This general method was further developed by Ruechardt and Hassmann (Ger. Offen. No. 2,155,545 (1973); Chem. Commun. 1972, 375), who prepared substituted indazoles by the nitrosation of substituted 2-methyl-o-toluidines using an alkyl nitrite or externally-generated nitrogen oxides. This process requires the use of an inert organic solvent, such as benzene or cyclohexane, together with an alkali metal salt of an alkanoic acid, for example, potassium acetate, and at least two molar equivalents of acetic anhydride to consume the water from the nitrosation and for reaction with the indazole compound as it is formed. The resulting 1-acetylindazole compound must be hydrolyzed prior to isolation of the free indazole product. When nitrogen oxides are used as the nitrosating agent, extra alkali metal alkanoate is required to neutralize the higher nitrogen oxides resulting by dismutation. In a modification of this work, which is described in Ger. Offen. No. 2,210,169 (1973), Ruechardt et al. used a glycol nitrite in the nitrosation step.

This invention relates to an improved process for the production of substituted indazoles. This one-step process, which can be used for the commercial production of haloindazoles, nitroindazoles, and certain other substituted indazoles, gives high yields of these compounds rapidly and efficiently. Unlike the previously-known procedures described hereinbefore, this process does not require the use of an inert organic solvent medium or an alkali metal alkanoate, and it does not employ sizeable excesses of the dehydrating agent. In addition, it does not include a step in which an acetylated indazole is hydrolyzed to give the desired product. A further advantage of this process is that it uses as the nitrosating agent an alkali metal nitrite or an alkaline earth metal nitrite rather than the more hazardous nitrite esters or externally-generated nitrous gases.

Nitrosation using the preferred sodium nitrite/acetic acid system also produces sodium acetate which forms with the acetic acid a buffer system that serves to maintain the reaction mixture at the level of acidity that is most favorable for the process to operate with minimum regulation. The sodium nitrite/acetic acid system is particularly well suited to the production of 5,7-dichloroindazole and trichloroindazoles from the corresponding 2-methylchloroacetanilides because these 2-methylchloroacetanilides are readily synthesized by the nuclear chlorination of 2-methylacetanilide in glacial acetic acid. The in-situ processing of 2-methylacetanilide through the 2-methylchloroacetanilides to the chloroindazoles without isolation of intermediate products is practical and economical.

In the process of this invention, a substituted 2-methylacetanilide is reacted with an alkali metal nitrite or an alkaline earth metal nitrite, which is preferably sodium nitrite, in a reaction medium that comprises an alkanoic acid having 2 to 4 carbon atoms and a dehydrating agent at a temperature above 50° C. The reaction that takes place is shown in the following equations:

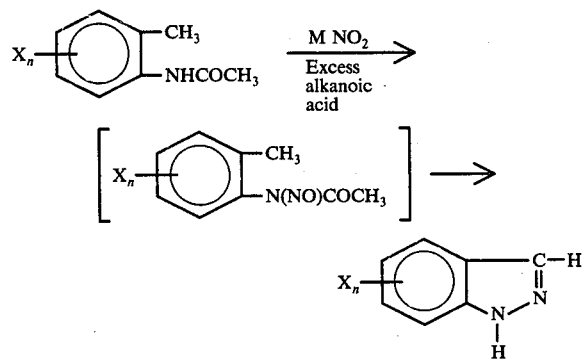

The indazole that is formed is separated from the reaction mixture, washed free of salts and reaction by-products, and dried.

The process of this invention can be used in the preparation of substituted indazoles that have the structural formula

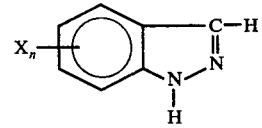

wherein X represents chlorine, bromine, iodine, fluorine, trichloromethyl, tribromomethyl, triiodomethyl, trifluoromethyl, nitro, —SO$_2$R, cyano, acetyl, butyryl, acetamino, propionamino, benzamino, or —COOR'; R represents hydroxyl, chlorine, bromine, fluorine, iodine, alkyl having 1 to 12 carbon atoms, chloroalkyl having 1 to 12 carbon atoms, bromoalkyl having 1 to 12 carbon atoms, iodoalkyl having 1 to 12 carbon atoms, fluoroalkyl having 1 to 12 carbon atoms, monoalkylamino, dialkylamino, phenyl, chlorophenyl, bromophenyl, iodophenyl, fluorophenyl, nitrophenyl, or alkylphenyl wherein the alkyl group has 1 to 4 carbon atoms; R' represents hydrogen, chlorine, bromine, fluorine, iodine, alkyl having 1 to 12 carbon atoms, chloroalkyl having 1 to 12 carbon atoms, bromoalkyl having 1 to 12 carbon atoms, iodoalkyl having 1 to 12 carbon atoms, fluoroalkyl having 1 to 12 carbon atoms, phenyl, chlorophenyl, bromophenyl, iodophenyl, fluorophenyl, nitrophenyl, or alkylphenyl wherein the alkyl group has 1 to 4 carbon atoms; and n represents a number in the range of 1 to 4.

Illustrative of these substituted indazoles are the following: 4-nitroindazole, 5-nitroindazole, 6-nitroindazole, 7-nitroindazole, 5,7-dinitroindazole, 7-chloroindazole, 4,7-dichloroindazole, 5,7-dichloroindazole, 4,5,7-trichloroindazole, 4,5,6-trichloroindazole, 4,5,6,7-tetrachloroindazole, 5-trichloromethyl-7-chloroindazole, 6-nitro-7-chloroindazole, 7-bromoindazole, 5,7-dibromoindazole, 4,5,6,7-tetrabromoindazole, 4,7-diiodoindazole, 5,7-difluoroindazole, 4-chloro-7-trichloromethylindazole, 7-tribromomethylindazole, 5-iodo-7-triiodomethylindazole, 7-trifluoromethylindazole, 5,7-dimethylaminoindazole, 5-(benzenesulfonyl)-indazole, 6-(chlorohexylsulfonyl)indazole, 5,6-di(butylsulfonyl)-indazole, 6-(p-toluenesulfonyl)indazole, 4,6-di(nitrobenzenesul-fonyl)indazole, 5,6-dicyanoindazole, 4,5,7-triacetylindazole, 5,7-diacetaminoindazole, 7-benzaminoindazole, 5,7-dicarbomethoxyindazole, 4,7-dicarboethoxyindazole, 7-carbophenoxyindazole, 5,7-dicarboxyindazole, and the like.

When the X substituent on the aromatic nucleus of the 2-methylacetanilide is strongly electronegative, for example, nitro(—NO$_2$), the nitrosation/ring closure reaction is readily effected regardless of the position of the substituent on the aromatic nucleus, the number of such substituents, and the presence of other substituents. When the substituent represented by X is either weakly electronegative or electropositive, for example, halogen, the substituent must be in a position adjacent to the acetamido (—NHCOCH$_3$) group, that is, in the 6-position of the aromatic nucleus, if a satisfactory yield of the desired indazole is to be obtained. Particularly good results are obtained when there are two or more of these substituents on the ring. Thus, it has been found that best results are obtained when the substituted acetanilide has either the structural formula

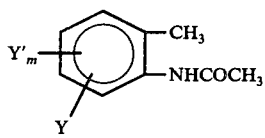

wherein Y represents a strongly electronegative substituent, such as nitro, —SO$_2$R, or cyano; Y' represents halogen, trihalomethyl, or —COOR'; R and R' have the aforementioned significance; and m represents a number in the range of 0 to 3, or the structural formula

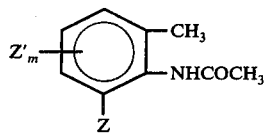

wherein Z represents a weakly electronegative substituent or an electropositive substituent, such as halogen, trihalomethyl, acoyl, acoylamino, aroylamino, or —COOR; Z' represents halogen, trihalomethyl, —COOR, nitro, or —SO$_2$R; and R, R', and m have the aforementioned significance.

In this one-step process for the production of substituted indazoles, an alkali metal nitrite or an alkaline earth metal nitrite, for example, sodium nitrite, potassium nitrite, barium nitrite, calcium nitrite, or strontium nitrite, is added to a reaction mixture that contains the appropriate 2-methylacetanilide, an alkanoic acid having 2 to 4 carbon atoms, and a dehydrating agent until 1.0 mole to 1.5 moles of the nitrite has been added per mole of the 2-methylacetanilide in the mixture. The nitrosation/ring closure reaction is usually and preferably carried out by adding solid sodium nitrite in the amount of 1.2 to 1.3 moles per mole of the 2-methylacetanilide portionwise to the reaction mixture which is being maintained at a temperature between 50° C. and its reflux temperature, which is generally about 120° C. A reaction temperature between 70° C. and 100° C. is preferred because it provides a sufficiently rapid rate of reaction while allowing for the monitoring of the acidity of the system.

The reaction mixture to which the alkali metal or alkaline earth metal nitrite is added contains the appropriate 2-methylacetanilide, from 1 part to 20 parts by weight of an alkanoic acid having from 2 to 4 carbon atoms per part by weight of the 2-methyl acetanilide, and from about 1.0 mole to 1.5 moles of a dehydrating agent per mole of the 1-methylacetanilide. It preferably contains from 2 parts to 10 parts by weight of the alkanoic acid per part by weight of the 2-methylacetanilide and from 1.0 mole to 1.2 moles of the dehydrating agent per mole of the 2-methylacetanilide.

The alkanoic acid in the reaction medium functions both as a solvent and as the primary acidifying agent for generating nitrous acid from the nitrite that is added. In most cases, the alkanoic acid is acetic acid because of its low cost and because it combines with the sodium acetate formed during the addition of sodium nitrite to form an anhydrous buffer system that is ideal for the nitrosation reaction. The use of acetic acid also permits the use of such dehydrating agents as acetic anhydride, polyphosphoric acid, and boron oxide without compatibility problems.

During the addition of the nitrite, the acidity of the reaction is monitored using a pH meter that is capable of measuring both pH and redox potential. For example, a Beckman Zeromatic SS-3 pH Meter or a Beckman Century SS-1 pH Meter may be used. Any electrode system that includes separate glass or metallic electrodes coupled with a reference electrode and that is capable of operating at temperatures up to 100° C. may be used with the pH meter. During the addition of the nitrite, the millivolt potential of the reaction mixture is maintained in the range of 250 mv. to 450 mv. In general, +MV potentials below this range inhibit N-nitrosation by protonating the amide substrate to a less reactive cationic-like species (—NH$_2$ ± COCH$_3$), while too basic a medium (450 mv. to 500 mv.) leads to an unfavorable equilibrium for the formation of the nitrous acid required for nitrosation. When the reaction mixture contains acetic acid, the normal anhydrous acetic acid/sodium acetate buffer range, which corresponds to a +MV potential range of 400 mv. to 440 mv., is preferred. The initial acidity level of the reaction mixture, which is usually below 300 mv., can be brought to the preferred range by the addition of sodium acetate. During the course of the reaction, the sodium nitrite that is added also contributes to sodium acetate buildup. The acidity of the reaction mixture can be maintained at the desired level during the course of the reaction by the addition of the necessary amounts of an anhydrous acid, such as sulfuric acid, polyphosphoric acid, phosphoric acid, trifluoroacetic acid, or hydrogen chloride.

When the addition of the nitrosating agent has been completed, the substituted indazole that has been formed is recovered from the reaction mixture and purified using conventional techniques. For example, after the acetic acid or other alkanoic acid has been removed from the reaction mixture by distillation, the residue can be added to a large volume of water to precipitate the crude product. This product can then be washed with water and extracted with dilute sodium hydroxide solution to remove salts and other reaction by-products from it.

When there are stable, non-reducible substituents, such as halogen or trihalomethyl, on the benzene ring, the crude substituted indazole may be treated with a reducing agent, such as sodium hydrosulfite, to convert nitro and nitroso substituted by-products to amine derivatives that are soluble in strong aqueous acid. In this way, the substituted indazole product can be upgraded with possible regeneration of an additional amount of the product.

In a preferred embodiment of the invention, the starting material is a substituted o-toluidine. In this process, the o-toluidine is reacted with a stoichiometric excess of glacial acetic acid and acetic anhydride to form a reaction mixture that contains the corresponding 2-methylacetanilide as well as acetic acid and acetic anhydride. Sodium nitrite or another alkali metal or alkaline earth metal nitrite is added to this reaction mixture to effect nitrosation and ring closure and thereby form the corresponding substituted indazole.

In another preferred embodiment of the invention, o-toluidine is reacted with a stoichiometric excess of glacial acetic acid and acetic anhydride to form a reaction mixture that contains 2-methylacetanilide, acetic acid, and acetic anhydride. Chlorine is introduced into this reaction mixture until an average of from 1 gram atom to 4 gram atoms of chlorine has reacted per mole of 2-methylacetanilide. During the chlorination, the reaction mixture is maintained at a temperature in the range of about 50° to 100° C. The resulting 2-methylchloroacetanilides may then, without isolation or purification, be converted to the corresponding chloroindazoles. In a modification of this process, the 2-methylchloroacetanilides are separated from the reaction mixture and purified, for example, by washing, by recrystallization from nitroethane, methanol, N,N-dimethylformamide, or a mixture of these solvents, by treatment with activated carbon, or by other conventional techniques. The purified 2-methylchloroacetanilides are then mixed with glacial acetic acid and acetic anhydride to form a reaction mixture to which sodium nitrite is added to effect nitrosation and ring closure.

The substituted indazoles that are prepared by the process of this invention are useful as intermediates in the preparation of preservatives, dyestuffs, and pharmaceuticals. For example, they can be reacted with formaldehyde or a formaldehyde-yielding substance to form the corresponding N'-hydroxymethylindazoles, which are useful as bactericides, fungicides, and pesticides. The use of N'-hydroxymethyl-substituted indazoles as preservatives for latex paints and other aqueous compositions that are subject to deterioration resulting from bacterial action is disclosed in U.S. Pat. No. 3,814,714.

The invention is illustrated by the following examples.

EXAMPLE 1

A. To a mixture of 321 grams (3.00 moles) of orthotoluidine and 1800 grams of glacial acetic acid was added 330 grams (3.24 moles) of acetic anhydride over a period of 15 minutes during which the temperature was maintained at 50°–60° C. The mixture was heated at 70°–75° C. for 15 minutes and then maintained at this temperature while chlorine was bubbled through it at the rate of about 120 grams per hour. The chlorination was continued for 3.5 hours during which time about 2.0 gram atoms of chlorine reacted per mole of o-toluidine. The chlorinated reaction mixture was distilled at 50 mm. to a pot temperature of 80° C. About 1800 grams of acetic acid was recovered.

The residue was dissolved in 2000 grams of nitroethane at 90°–95° C., cooled with stirring to 10°–15° C. in 2 hours, filtered, and washed with 800 grams of cold (0°–5° C.) methanol. The product was air-dried to constant weight. There was obtained 458 grams of a mixture of methylchloroacetanilides, a white crystalline solid having the following composition as determined by gas chromatography:

2-Methyl-6-chloroacetanilide: 1.8%
2-Methyl-4,6-dichloroacetanilide: 79.3%
2-Methyltrichloroacetanilides (2 isomers): 14.2%
By-products: 4.7%

B. A 155 gram portion of this product was dissolved in a mixture of 1000 grams of methanol and 50 grams of N,N-dimethylformamide. The resulting solution was passed through a column containing 129 grams of activated carbon. The clear carbon-treated liquid was evaporated to a volume of about 100 ml. and then poured into 1 liter of water. The white solid that precipitated was collected and air-dried. There was obtained 129 grams of a product that contained the following components:

2-Methyl-6-chloroacetanilide: 1.1%
2-Methyl-4,6-dichloroacetanilide: 81.4%
2-Methyltrichloroacetanilides (2 isomers): 17.2%
By-products: 0.3%

When this product was recrystallized from nitroethane, there was obtained 98.4 grams of a product that contained the following components:

2-Methyl-6-chloroacetanilide: 0.4%
2-Methyl-4,6-dichloroacetanilide: 85.9%
2-Methyltrichloroacetanilides (2 isomers): 13.1%
By-products: 0.6%

C. To a mixture of 200 grams of glacial acetic acid and 16.0 grams (0.157 mole) of acetic anhydride was added a 34.0 gram portion of the aforementioned mixture of 2-methylchloroacetanilides, which contained 85.9% (0.134 mole) of 2-methyl-4,6-dichloroacetanilide. The resulting solution was heated at 90°–95° C. for about 2 hours while 13.0 grams (0.188 mole) of solid sodium nitrite was added to it portionwise. During the addition of the sodium nitrite, the acidity of the reaction mixture was monitored by means of a Beckman Zeromatic SS-3 pH Meter equipped with a Beckman 39013 probe combination electrode filled with 4M potassium chloride saturated with silver chloride, which was inserted into the reaction mixture. As the sodium nitrite was added, the +MV potential, which was initially below 300 mv., rose rapidly to about 400 mv. and was maintained between 420 mv. and 440 mv. by the addition of small amounts of a 50/50 (wt. wt.) mixture of 100% sulfuric acid and glacial acetic acid. The dark amber reaction product was heated at 50 mm. to 80° C. to recover 215 grams of acetic acid. The residue was poured into 250 grams of water; the slurry that formed was stirred at 70° C.–80° C. for a few minutes, cooled to 20°–25° C., and filtered. The product was washed with water and then treated with 500 grams of 5% sodium hydroxide solution at 90°–95° C. The resulting mixture was filtered and acidified to pH 2 with hydrochloric acid. The slurry that formed was cooled to 20°–25° C.

and then filtered. After washing with water and air-drying at 60°–70° C., 25 grams of a chlorinated indazole product was obtained. Gas chromatographic analysis of the corresponding trimethylsilyl derivatives indicated that the product contained the following components:
 7-chloroindazole: 0.8%
 5,7-dichloroindazole: 77.7%
 Trichloroindazoles (2 isomers): 10.3%
 By-products: 11.2%
The yield of 5,7-dichloroindazole from 2-methyl-4,6-dichloroacetanilide was 78.7%

To 15 grams of the product were added 80 grams of methanol, 8 grams of water, and 5 grams of sodium hydrosulfite. This mixture was heated at reflux temperature (69°–70° C.) for 1 hours, and then 400 grams of water was added to it. The product, which was isolated by filtration, was washed with water, air-dried, and reslurried in a mixture of 180 grams of methanol and 34 grams of 37% hydrochloric acid. This slurry was diluted with 500 grams of water, cooled to 20°–25° C., and filtered. The product, after washing with water and drying at 70°–80° C., weighed 14.4 grams and contained the following components:
 7-chloroindazole: 0.7%
 5,7-dichloroindazole: 85.8%
 Trichloroindazoles (2 isomers): 11.4%
 By-products: 2.1%

EXAMPLE 2

To a mixture of 28.3 grams (0.20 mole) of 2-methyl-6-chloroaniline and 150 grams of glacial acetic acid was added 41 grams (0.40 mole) of acetic anhydride over a period of 15 minutes during which the temperature of the reaction mixture was maintained at 50°–60° C. The amount of acetic anhydride added was that required for the acetylation of the 2-methyl-6-chloroaniline plus that required for the removal of water of reaction in the subsequent nitrosation step.

To the reaction mixture, which had been heated at 70°–75° C. for 15 minutes, was added 17.4 grams (0.25 mole) of solid sodium nitrite over a period of 90 minutes while the temperature was maintained at 90°–95° C. During the addition of the sodium nitrite, the +MV potential of the reaction mixture as measured by the pH meter described in Example 1 rose from 275 mv. to 330 mv. The reaction mixture was heated at 50 mm. to 80° C. to remove acetic acid from it and then poured into water. The resulting slurry was stirred at 70°–80° C. for a few minutes, cooled to 20°–25° C., and filtered. The product was washed with water and then treated with 5% sodium hydroxide solution at 90°–95° C. The resulting mixture was acidified to pH 0.5; after removal of insoluble tarry material, the pH of the mixture was brought to 4. The precipitated product was collected, washed with water, and dried. There was obtained 23.4 grams of an amber-colored solid that contained 93.5% of 7-chloroindazole and 6.5% of reaction by-products.

The yield of 7-chloroindazole from 2-methyl-6-chloroaniline was 76.6%.

EXAMPLE 3

A. A mixture of 100 grams of the product of Example 1A, which contained 79.3% of 2-methyl-4,6-dichloroacetanilide, with 500 grams of glacial acetic acid and 1 gram of iodine was stirred at 85°–90° C. for 8 hours while a total of 330 grams (4.65 moles) of chlorine was bubbled through it.

The chlorinated reaction mixture was sparged with dry air for a few minutes. Then 10 grams of sodium hypophosphite monohydrate was added to it. The resulting mixture was heated with stirring at 65°–70° C. for 2 hours to reduce the by-products that contained labile chlorine; it was then distilled at 50 mm. to a pot temperature of 80° C. to remove 475 grams of acetic acid. The residue was stirred with 300 grams of methanol at 60°–70° C. for 15 minutes, cooled to 10°–15° C., and filtered. The product was washed free of color with cold methanol, triturated with water, filtered, and washed with water. After air-drying, 71.6 grams of a white solid product was obtained that contained the following components:
 2-Methyl-4,6-dichloroacetanilide: 5.3%
 2-Methyl-3,4,6-trichloroacetanilide: 61.3%
 2-Methyl-4,5,6-trichloroacetanilide: 24.2%
 By-products: 9.2%

B. A mixture of 25.3 grams of the product of Ex. 3A, which contained a total of 85.5% of 2-methyltrichloroacetanilides, with 150 grams of glacial acetic acid and 11 grams of acetic anhydride was treated with 8.7 grams of sodium nitrite at 90°–95° C. During the addition of the sodium nitrite, the +MV potential as measured by the pH meter described in Example 1 rose rapidly to 410 mv. The crude product isolated after removal of acetic acid and drowning with water was a light buff-colored solid that weighed 21 grams and that contained the following components:
 5,7-dichloroindazole: 2.9%
 4,5,7-trichloroindazole: 35.5%
 5,6,7-trichloroindazole: 15.6%
 By-products: 46.0%
Treatment with aqueous sodium hydroxide of 18.3 grams of this crude product by the procedure described in Example 1C yielded 8.0 grams of an upgraded product that contained the following components:
 5,7-dichloroindazole: 3.7%
 4,5,7-trichloroindazole: 57.0%
 5,6,7-trichloroindazole: 23.7%
 By-products: 15.6%

EXAMPLE 4

The acetylation/chlorination of o-toluidine was carried out by the procedure described in Example 1A until 2.22 gram atoms of chlorine had reacted per mole of o-toluidine. The reaction product was shown by gas chromatography to have the following composition:
 2-Methyl-6-chloroacetanilide: 2.9%
 2-Methyl-4,6-dichloroacetanilide: 63.5%
 2-Methyl-3,4,6-trichloroacetanilide: 15.6%
 2-Methyl-4,5,6-trichloroacetanilide: 11.6%
 By-products: 6.4%
An aliquot of this product that corresponded to 0.53 mole of o-toluidine was mixed with 340 grams of glacial acetic acid and 52.7 grams of acetic anhydride, and the mixture was stirred at 70°–75° C. for 1 hour with 2.2 grams of sodium hypophosphite monohydrate to reduce by-products containing labile chlorine. The product obtained contained the following components:
 2-Methyl-6-chloroacetanilide: 3.7%
 2-Methyl-4,6-dichloroacetanilide: 64.7%
 2-Methyl-3,4,6-trichloroacetanilide: 15.6%
 2-Methyl-4,5,6-trichloroacetanilide: 12.9%
 By-products: 3.1%
This product was treated with 47 grams (0.68 mole) of sodium nitrite at 90°–95° C. by the procedure described in Ex. 1C. During the addition of the sodium nitrite, the +MV potential rose from 155 mv. to 360 mv. The product was purified by extraction with alkali and then treatment with sodium hydrosulfite by the procedures described in Ex. 1C. The yield and distribution of components in the alkali-treated product and in the subsequently-obtained hydrosulfite-treated product were as follows:

|  | Alkali-Extracted Product | Hydrosulfite-treated Product |
|---|---|---|
| Yield | 60.4% | 59.1% |
| Distribution of Components |  |  |
| 7-Chloroindazole | 1.6 | 0.5 |
| 5,7-Dichloroindazole | 58.5 | 64.8 |
| 4,5,7-Trichloroindazole | 11.8 | 13.4 |
| 5,6,7-Trichloroindazole | 9.0 | 10.1 |
| By-products | 19.1 | 11.2 |

EXAMPLE 5

A mixture of 30.4 grams (0.20 mole) of 2-methyl-4-nitroaniline, 150 grams of glacial acetic acid, and 41 grams (0.40 mole) of acetic anhydride was treated with 17.3 grams (0.25 mole) of sodium nitrite by the procedure described in Example 1C. During the addition of sodium nitrite, the +MV potential, which was originally 270 mv., rose rapidly to 430 mv. After it had been purified by treatment with 5% sodium hydroxide solution by the procedure described in Example 1C, the product, which was an amber-colored solid that weighed 22.7 grams, was found by gas chromatographic analysis to contain 89.3% of 5-nitroindazole and 11.7% of reaction by-products. The yield of 5-nitroindazole was 62.1%.

EXAMPLE 6

The conversion of 2-methyl-5-nitroaniline to 6-nitroindazole was carried out by the procedure described in Example 5. There was obtained a 96.1% yield of a product that contained 97.8% of 6-nitroindazole.

EXAMPLE 7

The conversion of 2-methyl-6-nitroaniline to 7-nitroindazole was carried out by the procedure described in Example 5. The product obtained contained 61.8% of 7-nitroindazole.

Each of the other substituted indazoles disclosed herein can be prepared similarly by the reaction of the appropriate 2-methylacetanilide with sodium nitrite in the presence of an alkanoic acid having 2 to 4 carbon atoms and a dehydrating agent at a temperature above 50° C.

What is claimed is:

1. In the process for the production of substituted indazoles having the structural formula

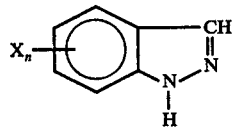

wherein X represents chlorine or nitro and n represents a number in the range of 1 to 4, by the reaction of a substituted o-toluidine with sodium nitrite to form a substituted N-nitroso-o-toluidine and the cyclization of said N-nitroso-o-toluidine wherein sodium nitrite is added to a reaction mixture that consists essentially of at least one acetanilide having the structural formula

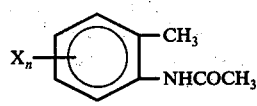

wherein X and n have the aforementioned significance, acetic acid, and acetic anhydride, said reaction mixture containing from 1 part to 20 parts by weight of acetic acid per part by weight of said acetanilide and from 1.0 mole to 1.5 moles of acetic anhydride per mole of said acetanilide, until from 1.0 mole to 1.5 moles of sodium nitrite has been added per mole of said acetanilide while maintaining the reaction mixture at a temperature between 50° C. and its reflux temperature, thereby forming a reaction product containing a substituted indazole, and thereafter separating the substituted indazole from the reaction product, the improvement wherein the reaction mixture to which sodium nitrite is added is formed by contacting a o-toluidine having the structural formula

wherein X and n have the aforementioned significance, with a stoichiometric excess of glacial acetic acid and acetic anhydride.

2. The process of claim 1 wherein the reaction mixture to which sodium nitrite is added is formed by contacting 2-methyl-6-chloroaniline with a stoichiometric excess of glacial acetic acid and acetic anhydride.

3. The process of claim 1, wherein the reaction mixture to which sodium nitrite is added is formed by contacting 2-methyl-4,6-dichloroaniline with a stoichiometric excess of glacial acetic acid and acetic anhydride.

4. The process of claim 1 wherein the reaction mixture to which sodium nitrite is added is formed by contacting 2-methyl-5-nitroaniline with a stoichiometric excess of glacial acetic acid and acetic anhydride.

5. The process of claim 1 wherein the reaction mixture to which sodium nitrite is added is formed by contacting a mixture comprising 2-methyl-4,6-dichloroaniline, 2-methyl-3,4,6-trichloroaniline, and 2-methyl-4,5,6-trichloroaniline with a stoichiometric excess of glacial acetic acid and acetic anhydride.

6. The process of claim 1 wherein the reaction mixture to which sodium nitrite is added is formed by
 (a) contacting o-toluidine with a stoichiometric excess of glacial acetic acid and acetic anhydride, thereby forming a first reaction mixture containing 2-methylacetanilide, acetic acid, and acetic anhydride and
 (b) contacting said first reaction mixture with chlorine until an average of from 1 gram atom to 4 gram atoms of chlorine has reacted per mole of 2-methylacetanilide, thereby forming a second reaction mixture containing 2-methylchloroacetanilides, acetic acid, and acetic anhydride.

7. The process of claim 6 wherein the 2-methyl-chloroacetanilides formed in Step (b) are separated from the second reaction mixture, recrystallized from a solvent selected from the group consisting of nitroethane, methanol, N,N-dimethylformamide, and mixtures thereof, and mixed with glacial acetic acid and acetic anhydride to form a third reaction mixture that contains 2 parts to 10 parts by weight of acetic acid per part by weight of the 2-methylchloroacetanilides and 1.0 mole to 1.2 moles of acetic anhydride per mole of the 2-methylchloroacetanilides.

8. The process of claim 6 wherein the second reaction mixture contains 2-methyl-6-chloroacetanilide, 2-methyl-4,6-dichloroacetanilide, 2-methyltrichloroacetanilides, acetic acid, and acetic anhydride.

9. The process of claim 6 wherein in Step (b) the first reaction mixture is maintained at a temperature between 50° C. and 100° C. during the chlorination to form the second reaction mixture.

* * * * *

UNITED STATES PATENT AND TRADEMARK OFFICE
CERTIFICATE OF CORRECTION

PATENT NO. : 4,096,333
DATED : Jun. 20, 1978
INVENTOR(S) : Eugene P. DiBella

It is certified that error appears in the above-identified patent and that said Letters Patent are hereby corrected as shown below:

Page 1, line 2, change "Di Billa" to -- DiBella --.

Page 1, line 5, Item [75], change "Di Billa" to -- DiBella --.

Signed and Sealed this

Sixteenth Day of January 1979

[SEAL]

Attest:

RUTH C. MASON
*Attesting Officer*

DONALD W. BANNER
*Commissioner of Patents and Trademarks*